(12) United States Patent
Migliori et al.

(10) Patent No.: US 6,844,722 B2
(45) Date of Patent: Jan. 18, 2005

(54) MUTUAL INDUCTANCE BRIDGE FOR DETECTION OF DEGRADATION IN METALLIC COMPONENTS

(75) Inventors: Albert Migliori, Santa Fe, NM (US); George W Rhodes, Corrales, NM (US)

(73) Assignee: Avistar, Inc., Albuquerque, NM (US)

( * ) Notice: Subject to any disclaimer, the term of this patent is extended or adjusted under 35 U.S.C. 154(b) by 336 days.

(21) Appl. No.: 10/107,317

(22) Filed: Mar. 28, 2002

(65) Prior Publication Data

US 2003/0030433 A1 Feb. 13, 2003

Related U.S. Application Data (60) Provisional application No. 60/310,828, filed on Aug. 9, 2001.

(51) Int. Cl.[7] ................................................. G01B 7/06
(52) U.S. Cl. ................... 324/207.19; 324/229; 324/240
(58) Field of Search ....................... 324/207.13, 207.15, 324/207.19, 228–229, 239–240

(56) References Cited

U.S. PATENT DOCUMENTS

| | | | |
|---|---|---|---|
| 2,418,686 A | 4/1947 | Zuschlag | |
| 3,422,346 A | 1/1969 | Hammer | |
| 4,644,271 A | 2/1987 | Toth et al. | |
| 5,432,444 A | * | 7/1995 | Yasohama et al. .......... 324/240 |
| 2002/0027437 A1 | 3/2002 | Tasca | |

FOREIGN PATENT DOCUMENTS

| | | |
|---|---|---|
| DE | 408640 | 1/1925 |
| FR | 2 065 234 A | 7/1971 |

* cited by examiner

*Primary Examiner*—Bot LeDynh
(74) *Attorney, Agent, or Firm*—Snider & Associates; Ronald R. Snider

(57) ABSTRACT

An inductive bridge circuit using mutual inductances to transform impedances is used for detection of wall-thinning defects in metals. The bridge circuit has a first test coil placed adjacent to a good metal section and a second test coil placed adjacent to a metal to be tested. The bridge circuit compares the inductance in the first coil and inductance in the second test coil to compare wall thinning defects. The apparatus may also include first and second measuring transformers which are connected between the bridge circuit and the test coils where the transformers provide for impedance matching and reduced current requirements in the bridge. The circuit may also include one or more potentiometer circuits connected across the bridge which are used for compensating for imbalance of impedance between the first and second test coils when the coils both have known good metal sections adjacent to them.

26 Claims, 10 Drawing Sheets

MUTUAL INDUCTANCE BRIDGE FOR DETECTION OF DEGRADATION IN METALLIC COMPONENTS

This application claims the priority of U.S. Provisional Application No. 60/310,828 filed on Aug. 9, 2001, which is incorporated herein by reference.

BACKGROUND OF THE INVENTION

(1) Field of the Invention

This invention relates to nondestructive testing for defects in metals and more particularly, for defects in boiler tubes or water walls used in the electric utility industry. More particularly, this invention is used for detection of erosion which occurs as a result of abrasive particles contained in coal feedstock. The erosion may be both internal and external. This invention provides a nondestructive inductance-based test technique that reliably assesses tube or wall thinning conditions and, thus, enables the prediction of future failure events.

(2) Description of Related Art

In the prior art, nondestructive techniques for measuring boiler tube erosion or water wall erosion comprise eddy-current testing, dye-penetrant testing, ultrasound testing, and x-ray testing. These systems are not cost effective because they are extremely slow, require use of delicate instruments which are incapable of survival in an industrial setting, require instruments which are very expensive, and use instruments which require highly skilled operators. It has been found that when using such prior art techniques, they are not cost effective for performing near 100% effective tests for some defects in large industrial systems even though such defects usually cause very costly failures when they occur.

BRIEF SUMMARY OF THE INVENTION

Erosion of the exterior walls occurs because of the abrasive particles contained in the coal feedstock. Primarily external corrosion is produced by these abrasive particles. Internal corrosion is caused by defective water chemistry combined with thermal cycling. Fortuitously, external wall erosion almost never occurs on the ends of tubes, allowing for a comparative examination with chafed sections. New boiler tube wall thickness ranges from 0.165 to 0.30 inches, depending on the required function. Many different steel and iron materials are often employed in a single plant, exacerbating the requirements for any test technique. Unanticipated boiler failures, caused by the breakout of a thin wall, account for almost one half of all coal fired power plant outages. Due to the importance reliable electric production, these outages represent a major limiting factor in the available generating capacity. To compensate, extra generating capacity has been installed to ensure that user needs are met. In the event that production falls short of demand, rolling blackouts become routine. Analysis of boiler tube failures shows the repetitive nature of these events. That is, following an economizer failure, several additional economizer failures are likely to occur in close proximity. A nondestructive test technique that reliably and rapidly assesses tube thinning conditions, thus predicting future failure events, can play a major role in mitigating avoidable downtime incidents.

Several known defects can be present in economizers. Spiral wound finned tubes can sometimes contain incomplete welds. The Mutual Inductance Bridge of this invention does not purport to distinguish this problem. One of the most prevalent faults is called the sawtooth defect. In this case, aerodynamic flow of gasses cause material to be eroded unevenly between the fins and only in a small area facing the direction of flow. This defect is only visible when the interstitial space is free of debris and the tube is viewed orthogonally. It results in a smaller amount of material removal than would be present with even wear and is exceptionally difficult to detect. But, the absolute wall thinning in one small area can lead to tube failure.

As an oversimplification, the Mutual Inductance Bridge of this invention detects the total mass of metal in the field of the interrogating coil and compares it to a reference. This explains why detection is limited to significant defects rather than pinholes, cracks and weld problems.

The basic physics behind the Mutual Inductance Bridge is determined by the "skin depth" of the effective electrically-conducting component. For a simple flat plate, the skin depth $\delta$ is:

$$\delta = [c/2\omega\sigma\mu]^{1/2}$$

where $\mu$ is the magnetic permeability, $\omega$ is the angular frequency, $\sigma$ is the electrical conductivity, and c is the speed of light. However, as the geometry differs from a flat plate, the effective skin depth changes. For complex structures, it is both difficult and not important to compute it, but it is useful to note the dependence on the various physical parameters. By using an appropriate frequency, the AC magnetic field can penetrate the tubing, and the electrical effect of the tubing is to modify the self inductance of the coil that is used to generate the magnetic field. The change in self-inductance L is a complex variable that depends on the total volume of metal in the effective region of the coil, its geometry, as well as $\mu$ (real changes in inductance) and $\sigma$ (imaginary changes in inductance, or, equivalently real changes in conductivity). For purposes of this invention, it is the sensitivity of L to the total volume and geometry of metal in the region of sensitivity of the coil that will enable detection of wall erosion or breaks. Unfortunately, substantial (that is, large enough to indicate replacement at a scheduled maintenance) changes in wall thickness arising from flame erosion for example, might change L by only a few percent. To detect reliably a 1% change in L is simple in a laboratory, but prohibitive in an electric utility boiler. Part of the problem is the environment where accurate instruments are subject to rough handling, temperature changes, and other problems caused by operators and the environment. Another important factor is that boiler tubes come from many different lots and from different manufacturers. Therefore, knowing an accurate value of L is a record keeping problem because the value of L for every lot of tubing, and its location in the plant must be known.

Measurement of a known "good" section of tube at each location, which can be found reliably with prior art methods, especially near an "end" allows one to compare readings of suspect sections to good ones. This process still requires very accurate readings, something that must be avoided if the defects a plant operator needs to find are to be detected, and a probable reason that such techniques are not in use.

There is, however, another approach that eliminates the need for an accurate measurement system. This approach is an Mutual Inductance Bridge circuit, where variation in inductance of each of two coils reflects differences in the tubing adjacent to the coils. It is common to define a mutual inductance bridge as a device for measuring mutual inductance. However, crucial to this invention is to use the principle of mutual inductance in the bridge itself, hence the name, to transform the impedances of search coils to values high enough to be readily detected using ordinary electrical instruments. Because the circuit is sensitive only to differences, various external perturbations, which are disastrous for the direct precision measurement of L, affect test and reference tubes equally, so that the bridge measurement becomes insensitive to these problems. The circuit elements perform the following functions:

DETAILED DESCRIPTION OF THE PREFERRED EMBODIMENT

Figure 1:
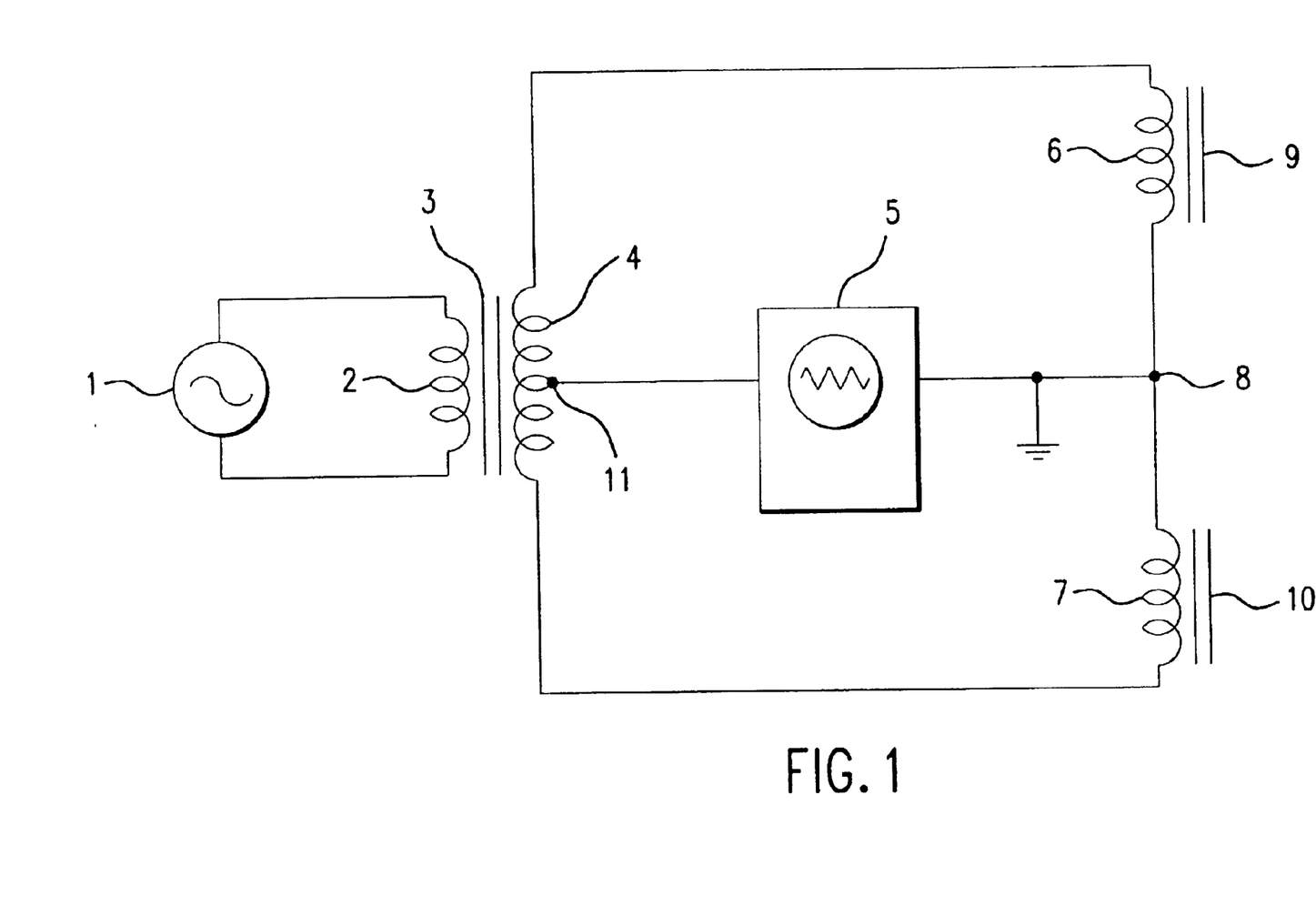
FIG. 1 shows an inductive bridge circuit for comparing inductance in a first metal section and a second metal section where the circuit includes no compensation for impedances.

In FIG. 1 there is shown the simplest form of a Mutual Inductance Bridge defect detection system of this invention. In this embodiment, an alternating current source (1) applies a voltage to an input coil (2) of a first transformer (3). The secondary (4) of the first transformer (3) is center tapped. The center tap (11) of the transformer secondary (4) is connected to an oscilloscope (5) which measures the voltage between the center tap (4) of the transformer (3) and ground. The oscilloscope (5), therefore, detects imbalances in the bridge circuit only. One side of the transformer (3) secondary (4) is connected to a first test coil (6) and the other side of the secondary (4) is connected to a second test coil (7). Test coils (6) and (7) are connected together at point (8) which is in turn connected to ground. As shown in FIG. 1, adjacent to each of test coils (6) and (7) are metallic portions (9) and (10). If the metallic portions (9) and (10) are absent, and if the first and second test coils (6) and (7) have equal impedances, and if each side of the secondary (4) of transformer (3) has equal impedances and mutual inductances with the primary, then the bridge circuit will be in balance and a zero voltage will be detected by oscilloscope (5). On the other hand, should inductor of test coils (6) and (7) not be identical, then a voltage will appear at oscilloscope (5). For example, should there be a metallic material portion (9) placed adjacent to the first test coil (6), then a voltage will appear at oscilloscope (5) reflecting the imbalance in the bridge produced by the change of impedance at the first test coil (6) produced by the change of inductance caused by the presence of the metallic portion (9). On the other hand, if an identical metallic portion (10) is placed adjacent to the second test coil (7), the bridge would once again be brought back into balance. However, as can be readily seen, this bridge provides a convenient apparatus for comparing a difference in metallic characteristics between the metal portions and (9) and (10) because any difference between the metallic portions changes the induction of first test coil (6) and second test coil (7).

Figure 2:
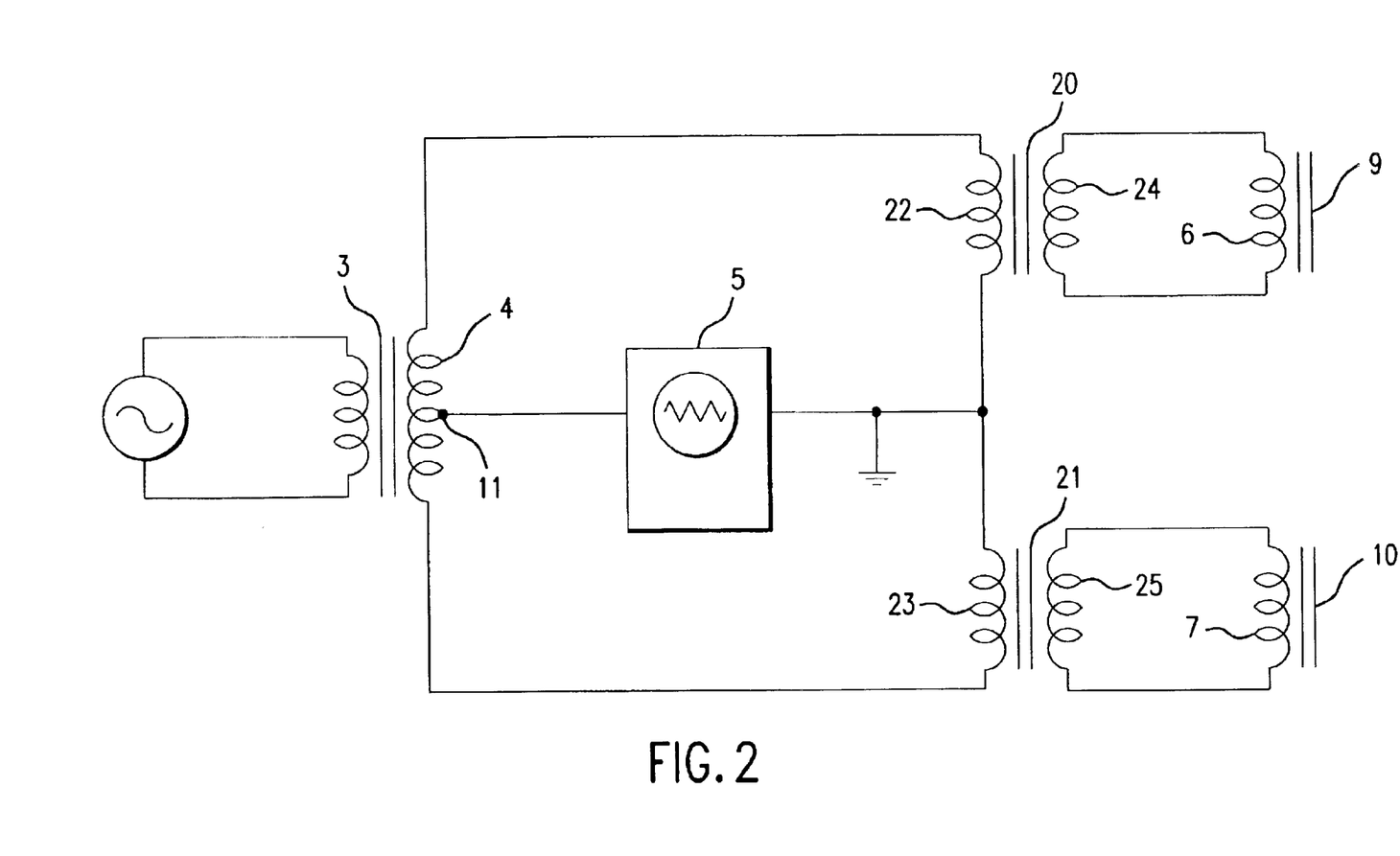
FIG. 2 shows an inductive bridge circuit similar to FIG. 1 except that transformers (mutual inductances) are used between the measuring coils and the inductive bridge circuit. Applicant shall call this a mutual inductance bridge.

In FIG. 2 there is shown an inductive bridge which is substantially identical to the bridge of FIG. 1, except that FIG. 2 includes transformers (20) and (21) placed in the bridge circuit, making it a mutual inductance bridge. The primaries (22) and (23) connect the first test coil (6) and second test coil (7) respectively to the bridge. Transformers (20) and (21) have a high number of turns on primaries (22) and (23) and a low number of turns on secondaries (24) and (25). The test coils (6) and (7) are placed across the secondary windings (24) and (25) and function like the test coils shown in FIG. 1. This step down relationship between the voltage in the mutual inductive bridge and the voltage across the first coil (6) and second coil (7) permits a higher current to flow in coils (6) and (7) without requiring a high current in the bridge circuit and a high current from the secondary (4) of transformer (3). Also, this allows the bridge circuit to operate at a higher voltage, thereby making the circuit more sensitive to changes in the inductance of the first and second test coils (6) and (7). Ideally, transformers (22) and (23) should be identical. The high bridge voltage also allows the windings of the bridge to be smaller and reduces the current in the secondary (4).

Figure 3:
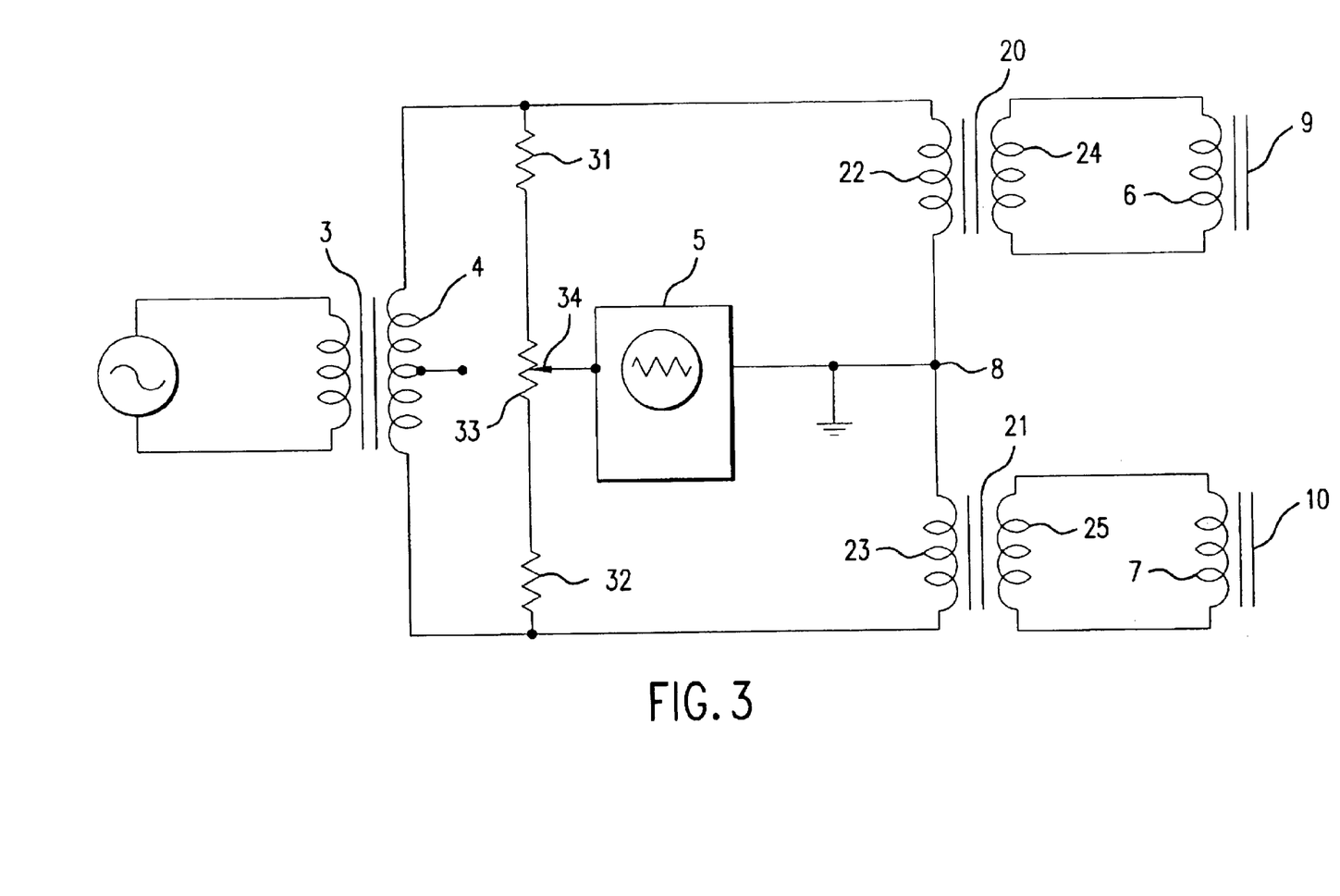
FIG. 3 shows an inductive bridge circuit of FIG. 1, which has been modified to include a potentiometer circuit across the secondary of the input power transformer and a wiper arm connected to the voltage measuring device. This arrangement provides for reduction of signal to noise ratio.

In FIG. 3 there is shown mutual inductance bridge circuit which is similar to bridge circuit (2). Like elements have been given the same reference numerals. The difference between FIG. 3 and FIG. 2 is the inclusion of a circuit for compensating for imbalance of impedance between the first and second test coils (6) and (7) and their associated circuit elements. This circuit comprises a first resistor (31) and a second resistor (32) which are connected to a potentiometer (33). Potentiometer (33) has a wiper connected to an input of the oscilloscope (5). When two identical metallic portions (9) and (10) are placed adjacent to coils (6) and (7) in the same related positions, the bridge circuit will indicate a minimum voltage at oscilloscope (5). This is the case in the circuit shown in FIG. 2. However, differences in impedance of circuit elements such as first test coil (6), second test coil (7) and transformers (20) and (21) can cause an unacceptable imbalance even when metallic portions (9) and (10) are identical and placed adjacent to the test coil (6) and (7) in an identical manner. The additional potentiometer (33) shown in FIG. 3 is used to balance any inductive difference read by the oscilloscope (5) when metallic portions (9) and (10) are identical and placed adjacent to the test coil (6) and (7) in an identical manner. Once the potentiometer is set at a point where the oscilloscope (5) reads a minimum voltage, then the circuit of FIG. 3 is ready to make measurements of an unknown metal portion. In the unknown measurement procedure, the metal portion (10) would be replaced with an unknown portion, and the unknown portion would be compared to the metallic portion (9). During this comparison, the difference becomes attributable only to the difference in the metals because the inductive errors (differences) that reside in the circuit would have been previously nulled out or compensated for by the adjustment of the position of the wiper (34) of potentiometer (33).

Figure 4:
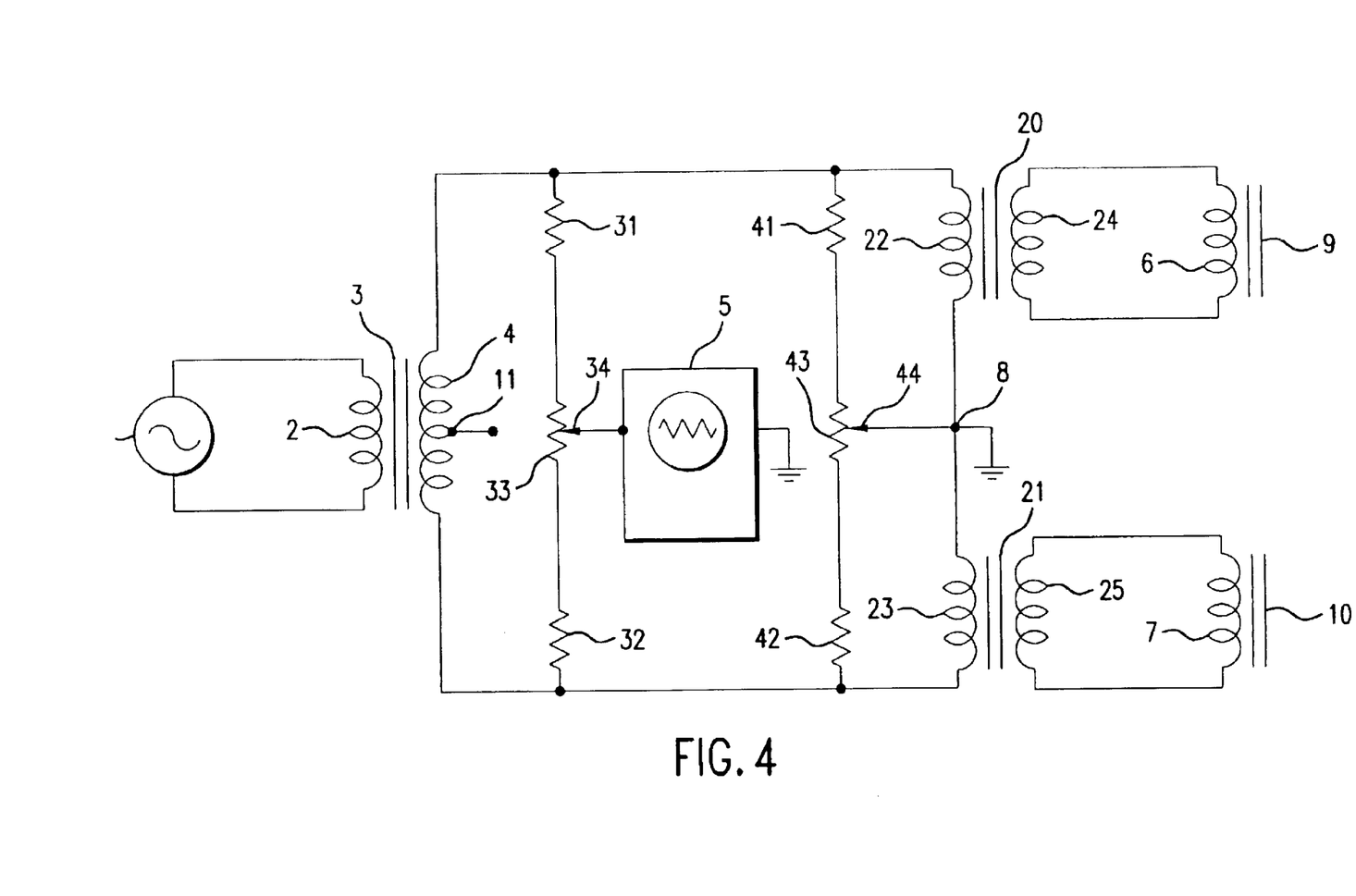
FIG. 4 shows a second potentiometer which is placed across the secondary of the input transformer and where the wiper arm of the potentiometer is connected to ground.

In FIG. 4 there is shown another mutual inductance bridge circuit similar to FIGS. 2 and 3 where like elements have been given the same reference numbers. FIG. 4 includes all of the elements of FIG. 3 including the potentiometer (34) which is used for balancing the inductive difference. FIG. 4, however, also includes a second impedance balancing potentiometer (43) connected to resistors (41) and (42). Potentiometer (43) has a wiper (44) connected to ground. In this configuration, one side of the oscilloscope (5) is connected to ground as in FIG. 3, and also the connection between transformer primaries (22) and (23) is also connected to ground. The potentiometer (43) also has its wiper (44) connected to ground as shown. When the potentiometer wiper (44) is adjusted to provide a minimum voltage at oscilloscope (5) while there are identical metallic portions (9) and (10) placed adjacent to test coils (6) and (7), there is provided for imbalance in the resistance of the circuitry. When potentiometer (44) is set to a position where oscilloscope (5) reads a minimum, the resistance differences in the transformers, or the test coils (6) and (7) as well as the bridge circuit are compensated for.

The bridge may also be constructed to eliminate the inductive balancing potentiometer (34) and its associated resistors (31) and (32) while maintaining the resistance balancing potentiometer (43) its wiper (44) and its associated (41) and (42). In this embodiment, the imbalance and resistance can be compensated for, but the imbalance of inductance cannot be compensated for. Also, in this situation, the input lead to the oscilloscope (5) not connected to ground would be connected to the center tap (11) of the secondary (4) of transformer (3) as shown in FIGS. 1 and 2.

Figure 5:
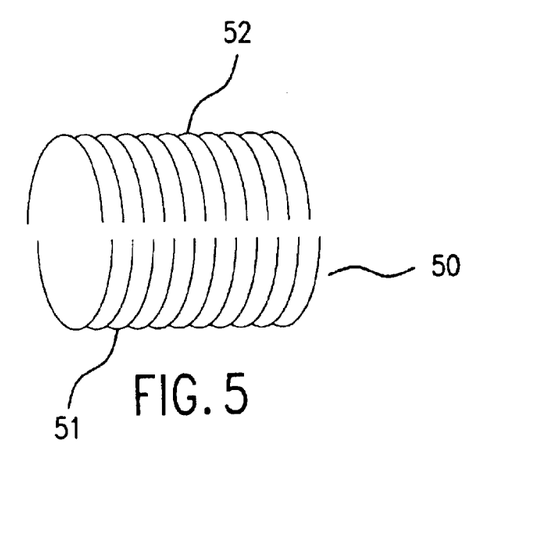
FIG. 5 shows a split coil arrangement for providing a coil adjacent to a metallic tube section.

In FIG. 5 there is shown a split coil (50). The split coil (50) allows the inductive bridge to be used to measure metal in tubular structures. Each half of the coil is placed against the metallic material to be measured (9) and the tips of the split coil are brought into contact, thereby forming a coil which wraps around the metallic material to be tested in a conventional manner. In the split coil concept of FIG. 5, the coil is fabricated with bayonet joints so that it can be inserted over a heat exchanger (2).

The main split search coils are coils (51) and (52). Each coil is 14 turns of #10 Cu wire wound in two layers, which are close wound on a 12 cm diameter mandrel. The details of the split coil are shown in FIG. 5.

Figure 6:
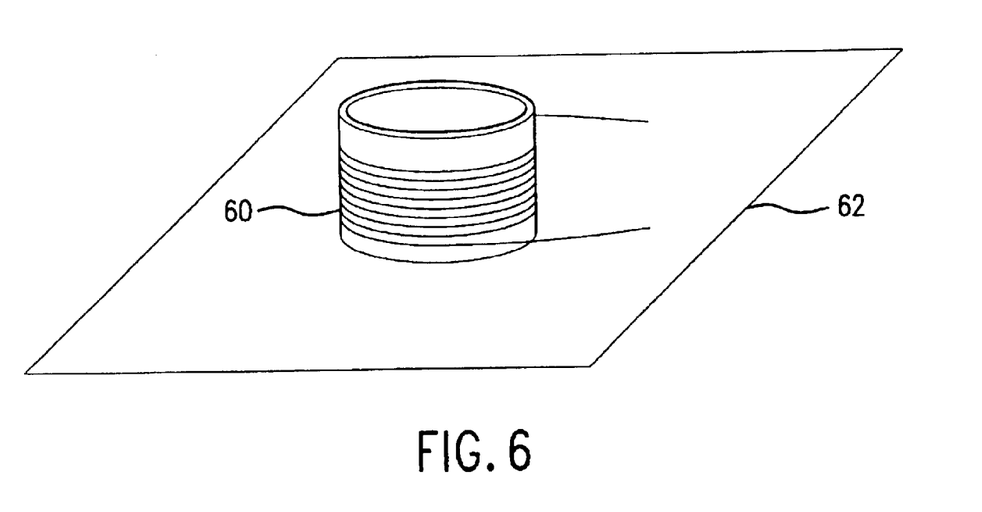
FIG. 6 shows a flat coil wound around a cylindrical form resting on a metallic sheet or water wall.

In FIG. 6 there is shown another embodiment were a test coil (60) is wrapped around a cylindrical body (which may or not be magnetic) and placed adjacent to a plate (62). In this configuration, a difference in a metallic portion (62) and another metallic portion can be measured in the manner described with respect to the test circuits discussed with respect to FIGS. 1–4.

Transformers (22) and (23) are 120 VAC to 12 VAC, 25 amp 50–60 Hz power transformers. These enable the very low impedance of test coils (6) and (7) to be increased 100 fold, thereby greatly reducing the sensitivity of the system to stray magnetic fields and electrical noise. Without such impedance matching, the noise from a standard 40 W flourescent light fixture meters away renders the system useless. Transformers (6) and (7) provide 25 amps of alternating current to test coils (6) and (7) to ensure adequate excitation of ferromagnetic steel. For stainless steel and other non-ferromagnetic metals, lower excitation may be used, but there is no real advantage to this, because signal/noise ratio can be degraded at low drive levels.

The AC signal source (1) must be capable of providing 120 VAC at 60 Hz for steel tubing and 400 Hz for stainless steel tubing at 250 VAC. By using a sine-wave invertor and a storage battery, the system is completely portable and insensitive to the harmonic content of utility power. This allows the user to view harmonic voltages (frequencies) which indicate differences in impedance as shown in FIGS. 16 and 17 without noise.

Figure 8:
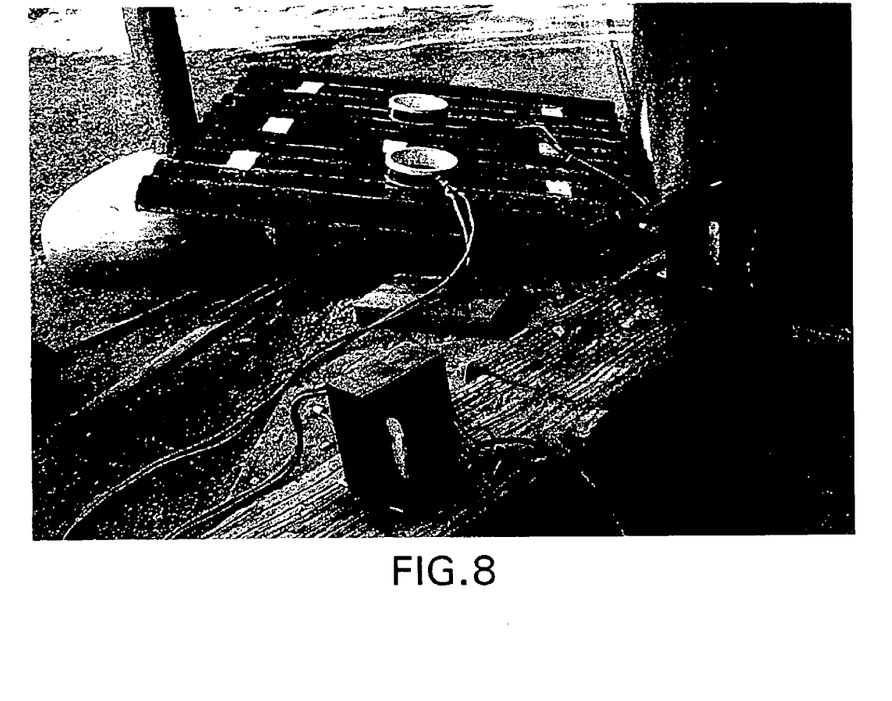
FIG. 8 shows actual test apparatus of a water wall arrangement with a pair of coils and transformers used during measurement.
Figure 9:
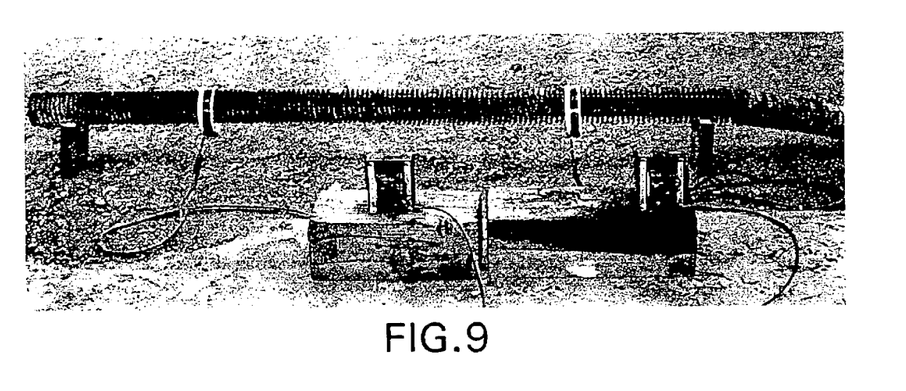
FIG. 9 shows an economizer tube with coils placed around it.
Figure 16:
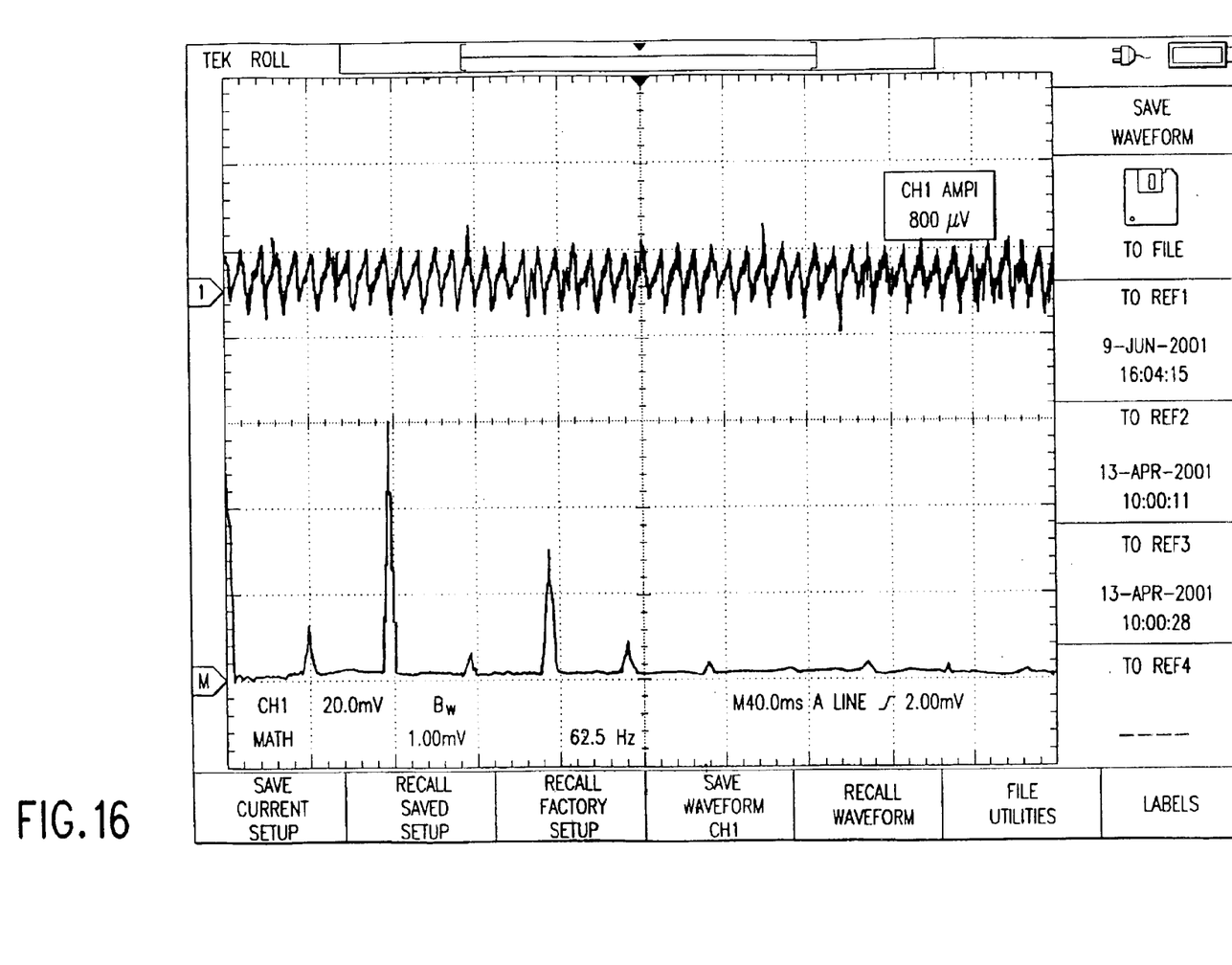
FIG. 16 shows an oscilloscope trace of an economizer when both sections are good. Here it should be noted that the second harmonic predominates and that the observed amplitude of the measured signal is low.
Figure 17:
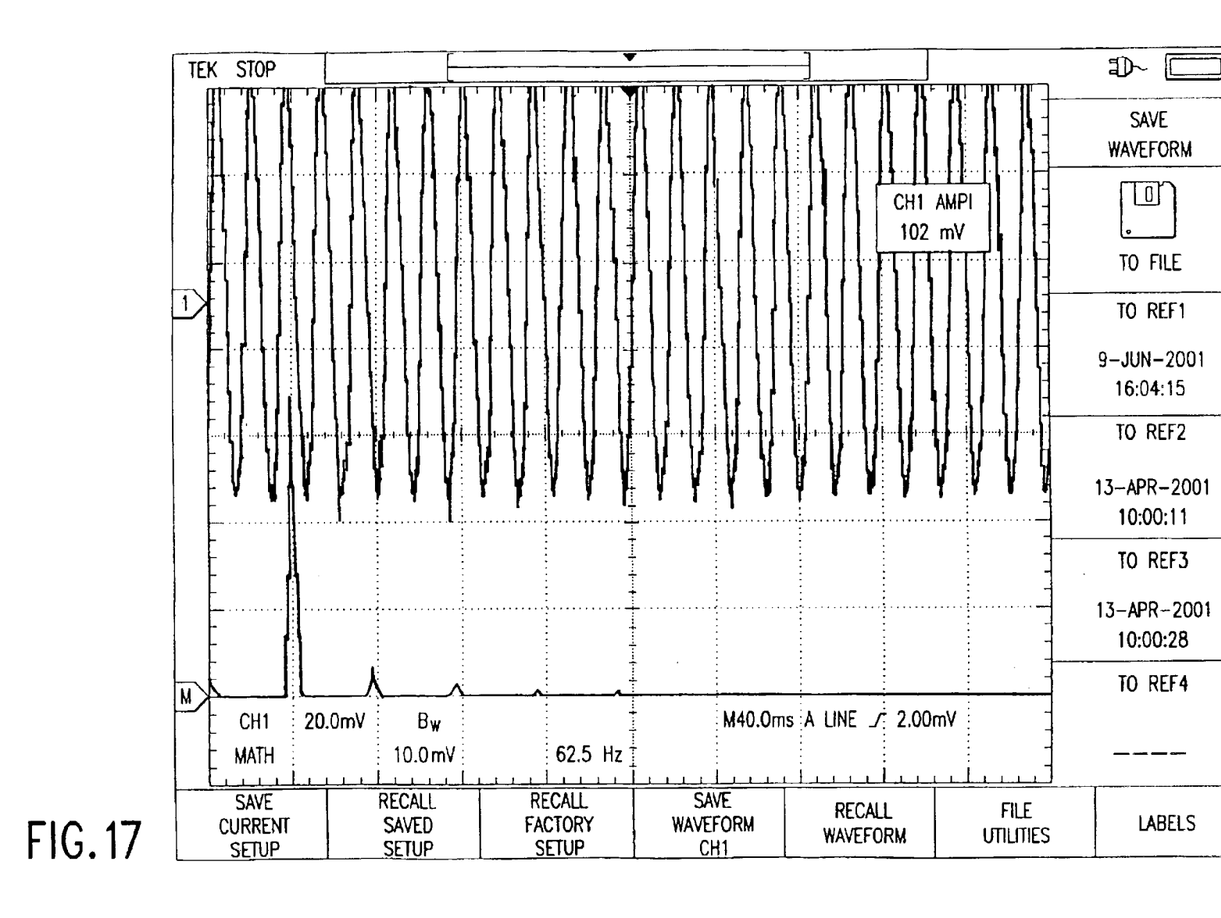
FIG. 17 shows a measurement taken of an economizer tube section where one section is bad. Here the first harmonic predominates and the amplitude is high as compared to the amplitude shown in FIG. 16.

The detector for this example is an oscilloscope (5) that can also provide the Fourier transform of the bridge signal as shown in the lower curves of FIGS. 16 and 17. To perform a test, test coil (9) is placed around an economizer tube, or aligned flush with the surface and centered over the joint between two water wall tubes as shown in FIG. 8. Test coil (7) is placed around the section to be tested (10) (FIG. 1) for economizers and above the section to be tested for water walls as shown in FIGS. 8 and 9. It is useful, but not necessary for test coil (9) to be on a good section because only differences will be detected, and if, by chance, test coil (9) begins on a bad section, then all good sections (presumably most of the system) will provide similar readings (FIG. 16) while defective sections will provide different reading. At this point, the two potentiometer wipers (34) and (44) (FIG. 4) are easily adjusted by the operator for a minimum signal on the scope. Applicant's experience has been that the minimum occurs when only second harmonic is visible as shown in FIG. 16.

The test setups for a water wall and economizer tubes are shown in FIGS. 9 and 8. Moderate care must be taken throughout the measurements to ensure that test coils (6) and (7) are coaxial within 1 cm and parallel to within 5 degrees over the economizer (FIG. 9), and flush and centered within 1 cm over a tube joint for the water wall (FIG. 8).

Figure 10:
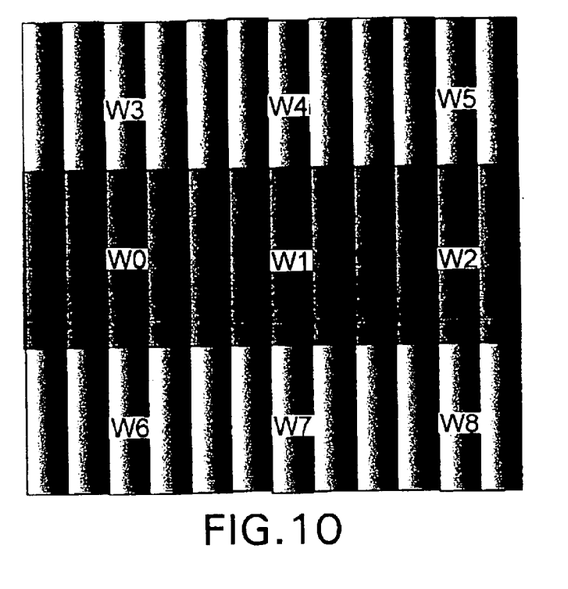
FIG. 10 shows a schematic sketch of the water wall test section with test sections labeled. W2 was a region with a ground flat 2.5 mm deep. Regions W0 and W1 show blackening and erosion.
Figure 11:
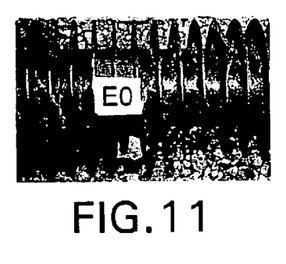
FIG. 11 shows an economizer section which is good.
Figure 12:
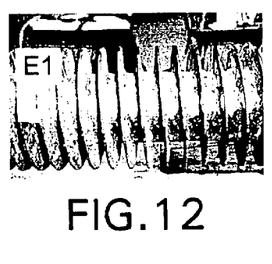
FIG. 12 shows an economizer section which is worn naturally from use.
Figure 13:
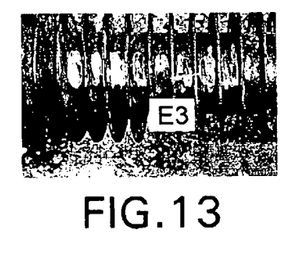
FIG. 13 shows an economizer section which has been ground at one section in order to remove material and provide comparison.

The defects that are detected are well defined for the economizer, but not as well defined for the water wall. This result is easily seen in FIG. 7 which shows that the signal is very low for good economizers and very high for bad ones (Examples 1–6). On the other hand, the minimum is generally higher for water wall measurements which provides for lower certainty of defects. For the water wall, a degraded and blackened area (W0, W1) is visible to the eye, shown schematically in FIG. 10. This area appears to be damaged, but in an ill-characterized manner. To assist with this understanding, Applicant ground flat a region 2.5 mm deep (W2) as well. Applicant also ground 2.5 mm from between several economizer fins (FIG. 13), just to compare a known sawtooth defect with the visible defect resulting from operational erosion (FIG. 12). In FIG. 10, Applicant shows a schematic diagram of the water wall test section with test points labeled and the blackened region shaded. The test points are W0, W1, . . . W8.

First the economizer is discussed. FIGS. 11–15 contain photographs of the test samples. The identification of good samples appeared obvious to the eye. Applicant used these to establish baselines for the intrinsic signal to noise as a function of normal product variations. Using a grinder, Applicant placed 2.5 mm defects in the interstitial region of a tube (E3) (FIG. 13) which had been previously characterized as "good". The increase in signal was immediately apparent. In addition, Applicant characterized the service-induced erosion (FIG. 12) as being about 2.5 mm deep and angled, and appearing on only the face toward hot air blast. In all cases, damage whether artificial or real, is readily apparent from Mutual Inductance Bridge data. More importantly, any of the damaged regions (FIGS. 12, 13) produce substantially larger (about 30 times) signals than do regions of known good economizer tubing. An example of a measurement of a bad economizer tube is shown in FIG. 17. In FIG. 17, the first harmonic becomes large as compared to the second harmonic which dominates for a good tube as shown in FIG. 16. This ratio (30:1) is the confidence ratio for economizer tests. It is quite likely that if several fins are bent there may also be an indication of damage using the Mutual Inductance Bridge even though no thickness errors (difference in amount of magnetic material) accompany it. A bent fin is obvious to an operator, who may make a judgement as to whether the geometrical defect masks important wall thickness defects or not. Note that these induced defects (FIG. 13), were of order ⅓ the wall thickness, and extended for only 1 to 2 cm of the 15 cm circumference of the tube. These defects are also of a size that is useful for a power plant operator to detect and take action. Note also that the signal/noise ratio is so good for these tests that an operator, or mechanical apparatus, can move the test coil at several meters per second and still obtain good results. More importantly, the Mutual Inductance Bridge provides a quantitative assessment of heat exchanger tubing that can be used to track erosion, and predict failures as data is acquired and understood.

Figure 14:
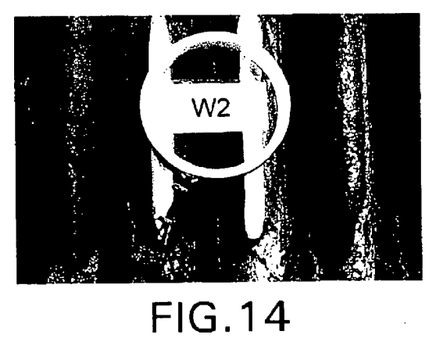
FIG. 14 shows a water wall portion where material has been ground away as a test baseline.
Figure 15:
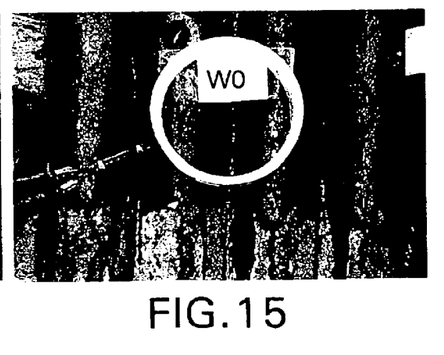
FIG. 15 shows an economizer wall where there is a blackened and eroded area.

Although the Mutual Inductance Bridge system was developed for economizer tube applications, it was applied to water walls yielding positive results. For water wall testing the coils were wound on a tube such as PVC pipe and placed adjacent to the wall as shown in FIGS. 14 and 15. FIGS. 14 and 15 and FIG. 10 show location of coils for water wall tests. Tests performed on the unmarred side away from flame, were presumed to present a pristine condition. For all water wall tests, the Mutual Inductance Bridge was adjusted once for the wear-side tests and once for the back side tests. It was clear that the unworn back side consistently produced very small signals, indicating very little variation over the entire surface. The worn front side was more complex. Because the biggest "good-section" signal was about 22 mV, the smallest bad section-signal may have been 43 mV, the margin from worst-case good-section signal to worst-case bad-section signal was only 2:1, as compared to 30:1 for the economizer. If example 11 (FIG. 7) (unknown condition) is discarded, then the defect produced a confidence ratio of 5:1. Although Applicant does not have adequate variant samples from which to generally quantify the technique, a detection of a 25% change of the original wall thickness would be cause for concern to the power plant.

Figure 7:
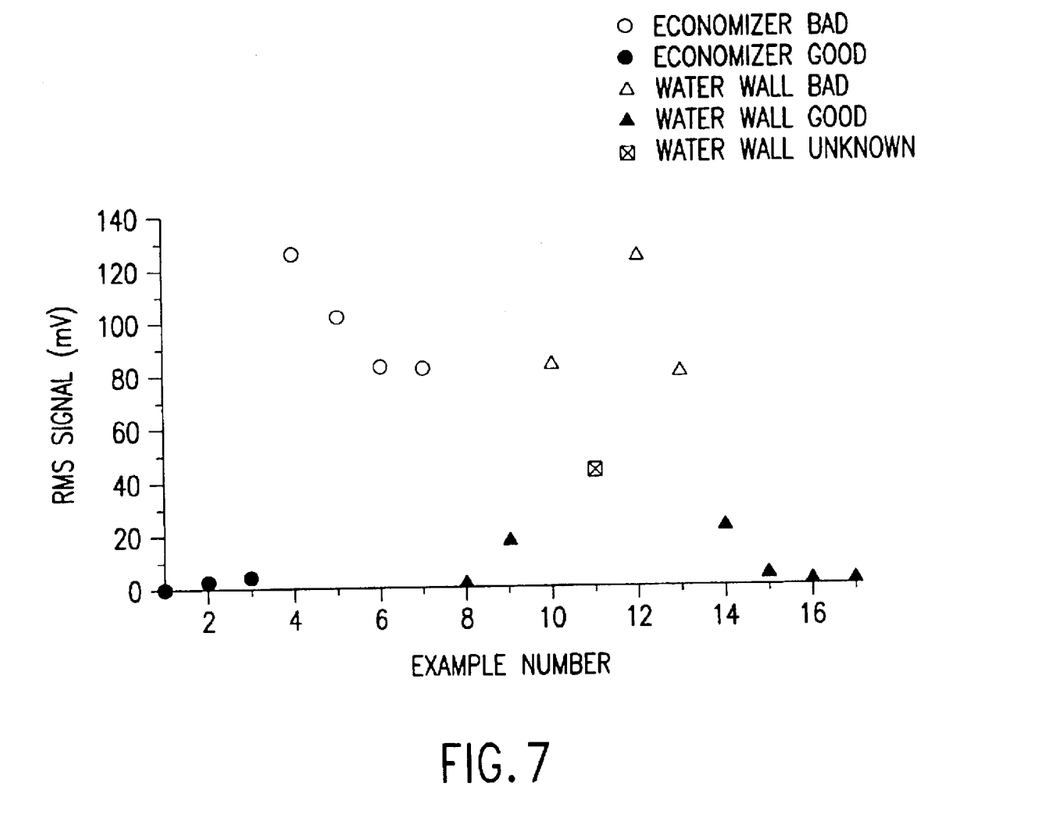
FIG. 7 shows a relationship between RMS voltages measured by an Mutual Inductance Bridge and coils placed on good and bad economizer tubes as well as good and bad water walls.

Overall conclusions may be reached by examining the corresponding plot (FIG. 7). The oscilloscope traces (FIGS. 16 and 17) show examples of a good and bad economizer tube test with the result that any RMS Mutual Inductance Bridge signal of about 40 mV appears to indicate a bad section of the exchanger. Also when the first harmonic begins to predominate, it indicates that there is an imbalanced and possibly bad tube.

One can also make inferences from FIG. 7 as to the total amount of missing metal that is detectable. This amount is of order 0.5 mm over the whole surface for the water wall, and about the same over the entire diameter for economizer. However, the single unknown-condition data point (Example 11) can change the water wall detection limits substantially in an unfavorable direction. Note also that a severely bent fin with only small amounts of wall erosion is shown as bad (Example 7).

A summary of the test results bases on the RMS Mutual Inductance Bridge signal. Plots for the fundamental are essentially the same. From this plot, it appears acceptable to define a bad section (either water wall or economizer) as anything with a signal above about 40 mV.

What is claimed is:

1. An apparatus for detection of wall-thinning defects of metals comprising:

a first test coil adjacent to a good metal section;

a second test coil adjacent to a metal to be tested;

a bridge circuit for comparing inductance in the first test coil and inductance in the second test coil; and wherein said bridge circuit comprises a transformer having a primary connected to a source of alternating voltage and having a center tapped secondary wherein each secondary winding is connected to one of said first and second test coils, said center tap is connected to an apparatus for measuring voltage and a connection between said first and second test coils is connected to the apparatus for measuring voltage.

2. An apparatus according to claim 1, wherein said source of alternating voltage has substantially no voltages under no load conditions which are higher in frequency than a fundamental voltage frequency.

3. The apparatus according to claim 1, wherein said apparatus for measuring voltage comprises an oscilloscope.

4. An apparatus for detection of defects of metals comprising:

a transformer having a secondary, said secondary having a center tap, and having a primary connected to a source of alternating current power;

a first test coil placed adjacent to good metal section;

a second test coil placed adjacent to a length of metal to be tested; and a voltage detection apparatus connected between said center tap and a connection between the first test coil and the second test coil;

wherein one side of the transformer secondary coil is connected to said first test coil and another side of the transformer secondary coil is connected to the second test coil.

5. The apparatus according to claim 4, wherein said voltage measuring device is an oscilloscope.

6. The apparatus in accordance with claim 4, wherein the connection between the first test coil, second test coil and voltage detection apparatus is connected to ground.

7. The apparatus in accordance with claim 6, wherein a difference in impedance between said first measuring transformer primary winding and said second measuring transformer primary winding is determined by a difference between a good metal section and a length of metal to be tested the good metal section and the metal section are to be tested are placed adjacent to in said first and second test coils.

8. An apparatus in accordance with claim 7, wherein said circuit for increasing a signal to noise ratio comprises as a circuit for compensating for imbalance of impedance between said first and second test coils.

9. An apparatus in accordance with claim 7, wherein said circuit for increasing a signal to noise ratio comprises a potentiometer connected across a power transformer secondary winding,
   wherein a wiper is connected from said potentiometer to an input of a voltage measuring device,
   wherein the voltage measuring device has a second connection to ground;
   a second potentiometer connected across the power transformer secondary winding having a wiper connected to ground; and
   wherein said first and second test coils are connected to each other and to ground.

10. The apparatus for detection of wall-thinning defects of metals comprising:
    a first test coil adjacent to a good metal section;
    a second test coil adjacent to a metal to be tested;
    a bridge circuit for comparing inductance in the first test coil and inductance in the second test coil; and
    further comprising a voltage measuring device which measures a voltage proportional to a difference in inductance of the first test coil and the second test coil.

11. The apparatus for detection of wall-thinning defects of metals comprising:
    a first test coil adjacent to a good metal section;
    a second test coil adjacent to a metal to be tested;
    a bridge circuit for comparing inductance in the first test coil and inductance in the second test coil, further comprising:
    a first measuring transformer connected to said first test coil;
    a second measuring transformer connected to said second test coil;
    wherein said first and second transformers each have primaries which comprise legs of said bridge circuit, and
    further comprising a voltage measuring device which measures a voltage proportional to a difference in inductance of the first test coil and the second test coil.

12. An apparatus for detection of wall-thinning defects of metals comprising:
    a power transformer having a primary connected to a source of alternating power and a secondary having a center tap;
    a first measuring transformer having a primary winding connected to a first end of said first transformer secondary winding and to ground, said first measuring transformer having a secondary winding connected to a first test coil;
    a second measuring transformer having a primary winding connected to a second end of said first transformer secondary winding and to ground, said second measuring transformer having a secondary winding connected to a second test coil;
    a voltage measuring apparatus for measuring voltage between the center tap of said first transformer and ground;
    a good metal section placed adjacent to one of said test coils and a length of metal to be tested placed adjacent to the other test coil;
    wherein a voltage measured by said voltage measuring apparatus indicates a difference in the impedance between the second transformer primary winding and that of the third transformer primary winding.

13. An apparatus for detection of wall-thinning defects of metals comprising:
    a first test coil adjacent to a good metal section;
    a second test coil adjacent to a metal to be tested;
    a bridge circuit for comparing inductance in the first test coil and inductance in the second test coil;
    further comprising a circuit for increasing a signal to noise ratio of said apparatus for detection wherein a metal to be tested is a good metal section and wherein a voltage across said bridge is reduced to a minimum.

14. An apparatus in accordance with claim 13, wherein said circuit for increasing a signal to noise ratio comprises a circuit for compensating for imbalance of resistance between said first and second test coils.

15. An apparatus in accordance with claim 14,
    wherein said circuit for increasing a signal to noise ratio comprises a potentiometer connected across a power transformer secondary winding, having a wiper connected to a voltage detection apparatus first terminal,
    wherein said voltage detection apparatus has a second terminal connected to ground, and
    wherein a connection between the first test coil and the second test coil is connected to ground.

16. An apparatus in accordance with claim 13, wherein said circuit for increasing a signal to noise ratio further comprises a circuit for compensating for imbalance of an inductance between said first and second test coils.

17. An apparatus for detection of wall-thinning defects of metals comprising:
    a first test coil adjacent to a good metal section;
    a second test coil adjacent to a metal to be tested; and
    a bridge circuit for comparing inductance in the first test coil and inductance in the second test coil, further comprising:
    a first measuring transformer connected to said first test coil;
    a second measuring transformer connected to said second test coil;
    wherein said first and second transformers each have primaries which comprise legs of said bridge circuit;
    further comprising a circuit for increasing a signal to noise ratio which comprises:
    a first potentiometer connected across a power transformer secondary winding, said potentiometer having a wiper connected to ground;
    a second potentiometer connected across said power transformer secondary winding, having a wiper connected to a voltage measuring apparatus;
    wherein said first and second measuring transformers each have a primary winding connected to said power transformer secondary winding;
    wherein said first and second measuring transformers each have a primary winding connected to ground; and
    wherein said voltage measuring apparatus has another terminal connected to ground.

18. A method for detection of wall-thinning defects of metals comprising the steps of:

placing a first test coil adjacent to a good metal section placing a second test coil adjacent to a good metal section connecting said first and second test coils in a bridge circuit for comparing inductance between the first coil and inductance in the second coil;

increasing a signal to noise ratio of said bridge circuit;

removing one of said good metal sections and replacing it with a section to be tested;

observing bridge voltage imbalance when a metal to be tested is placed adjacent to one of said test coils.

19. A method for detection of wall-thinning defects of metals in accordance with claim 18, further comprising the steps of:

connecting a first transformer to a source of alternating current power;

connecting said first test coil to a first measuring transformer;

connecting said second test coil to a second measuring transformer; and connecting primary windings of said first and second measuring transformers to a secondary winding of said first transformer.

20. A method for detection of wall-thinning defects of metals in accordance with claim 19, further comprising the steps of:

replacing the metal to be tested with a metal which is substantially identical to the good metal section;

adjusting a position of the wiper to a position where a voltage measured by said voltage measuring apparatus is a minimum.

21. A method for detection of wall-thinning defects of metals in accordance with claim 20, wherein said impedance at said measuring transformers includes impudence of said measuring transformers and said test coils.

22. A method for detection of wall-thinning defects of metals in accordance with claim 18, further comprising the steps of:

connecting a potentiometer across a secondary winding of said first transformer;

connecting a wiper of said potentiometer to a voltage measuring apparatus first terminal; and connecting a voltage measuring apparatus second terminal to a connection between said first and second measuring transformers.

23. A method for detection of wall-thinning defects of metals in accordance with claim 22, further comprising the steps of:

compensating the bridge for differences in impedance at said measuring transformers.

24. A method for detection of wall-thinning defects of metals in accordance with claim 19, further comprising the step of:

connecting the connection between said first and second measuring transformers to ground.

25. A method for detection of wall-thinning defects of metals comprising the steps of:

placing a first test coil adjacent to a good metal section placing a second test coil adjacent to a metal section to be tested connecting said first and second test coils in a bridge circuit comparing inductance between the first coil and inductance in the second coil by reducing voltage across said bridge circuit to a minimum.

26. A method for detecting of wall-thinning defects of metals in accordance with claim 25, further comprising using a source of alternating voltage which has substantially no voltages under no load conditions which are higher in frequency than a fundamental voltage frequency.

* * * * *